(12) United States Patent
Niimi et al.

(10) Patent No.: US 10,589,125 B2
(45) Date of Patent: Mar. 17, 2020

(54) BOLUS AND METHOD FOR PRODUCING SAME

(71) Applicants: Tatsuya Niimi, Kanagawa (JP); Yoshihiro Norikane, Kanagawa (JP); Takashi Matsumura, Kanagawa (JP); Hiroshi Iwata, Tokyo (JP); Hiroyuki Naito, Tokyo (JP)

(72) Inventors: Tatsuya Niimi, Kanagawa (JP); Yoshihiro Norikane, Kanagawa (JP); Takashi Matsumura, Kanagawa (JP); Hiroshi Iwata, Tokyo (JP); Hiroyuki Naito, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 16/058,527

(22) Filed: Aug. 8, 2018

(65) Prior Publication Data

US 2018/0345036 A1     Dec. 6, 2018

Related U.S. Application Data

(63) Continuation of application No. PCT/JP2016/086956, filed on Dec. 12, 2016.

(30) Foreign Application Priority Data

Mar. 14, 2016   (JP) ............................ 2016-049814
May 12, 2016   (JP) ............................ 2016-096429

(51) Int. Cl.
| | |
|---|---|
| *A61N 5/10* | (2006.01) |
| *B33Y 80/00* | (2015.01) |
| *A61K 41/00* | (2006.01) |
| *B33Y 10/00* | (2015.01) |

(52) U.S. Cl.
CPC ............ *A61N 5/10* (2013.01); *A61K 41/0038* (2013.01); *B33Y 80/00* (2014.12); *A61N 2005/1096* (2013.01); *B33Y 10/00* (2014.12)

(58) Field of Classification Search
CPC .............................................. A61N 2005/1096
See application file for complete search history.

(56) References Cited

U.S. PATENT DOCUMENTS

| | | | | |
|---|---|---|---|---|
| 5,402,783 A | * | 4/1995 | Friedman ........... | A61K 49/1803 378/65 |
| 6,231,858 B1 | * | 5/2001 | Izeki ...................... | C08B 37/00 424/1.69 |
| 2001/0049413 A1 | | 12/2001 | Haraguchi | |
| 2004/0106722 A1 | * | 6/2004 | Haraguchi ............. | A61L 15/60 524/445 |
| 2012/0271093 A1 | | 10/2012 | Fukumoto et al. | |
| 2015/0094838 A1 | * | 4/2015 | Mac Laverty ..... | G05B 19/4099 700/98 |
| 2016/0115297 A1 | | 4/2016 | Norikane et al. | |
| 2016/0275818 A1 | | 9/2016 | Norikane et al. | |
| 2017/0008228 A1 | | 1/2017 | Iwata et al. | |
| 2017/0239886 A1 | | 8/2017 | Norikane | |

FOREIGN PATENT DOCUMENTS

| | | | | |
|---|---|---|---|---|
| EP | 0 928 795 A2 | | 7/1999 | |
| EP | 1 160 286 A1 | | 12/2001 | |
| EP | 2 810 693 A2 | | 12/2014 | |
| JP | 62-204770 | | 9/1987 | |
| JP | 62-298376 | | 12/1987 | |
| JP | 03-115897 | | 5/1991 | |
| JP | 11-221293 | | 8/1999 | |
| JP | 11-221294 | | 8/1999 | |
| JP | 11221293 A | * | 8/1999 | ............... A61N 5/10 |
| JP | 11-255958 | | 9/1999 | |
| JP | 2000-292599 | | 10/2000 | |
| JP | 2002-053629 | | 2/2002 | |
| JP | 2006-028446 | | 2/2006 | |
| JP | 2014-227384 | | 12/2014 | |
| JP | 2015-136895 | | 7/2015 | |
| JP | 2015-138192 | | 7/2015 | |
| WO | WO2011/055670 A1 | | 5/2011 | |
| WO | WO 2015/077881 A1 | | 6/2015 | |
| WO | WO2015/111366 A1 | | 7/2015 | |

OTHER PUBLICATIONS

International Search Report dated Mar. 14, 2017 for counterpart International Patent Application No. PCT/JP2016/086956 filed Dec. 12, 2016 (with English Translation).
Written Opinion dated Mar. 14, 2017 for counterpart International Patent Application No. PCT/JP2016/086956 filed Dec. 12, 2016.
Extended European Search Report dated Feb. 11, 2019 in corresponding European Patent Application No. 16894582.2 citing documents AA, AO-AR therein, 7 pages.

* cited by examiner

*Primary Examiner* — Michael B. Pallay

(74) *Attorney, Agent, or Firm* — Oblon, McClelland, Maier & Neustadt, L.L.P.

(57) ABSTRACT

Provided is a bolus formed of a hydrogel, wherein the hydrogel includes water, a polymer, and a mineral, and wherein the bolus is applied to a patient who receives a radiation therapy.

16 Claims, 11 Drawing Sheets

BOLUS AND METHOD FOR PRODUCING SAME

CROSS-REFERENCE TO RELATED APPLICATIONS

The present application is a continuation application of International Application No. PCT/JP2016/086956, filed Dec. 12, 2016, which claims priority to Japanese Patent Application No. 2016-049814, filed Mar. 14, 2016 and Japanese Patent Application No. 2016-096429, filed May 12, 2016. The contents of these applications are incorporated herein by reference in their entirety.

BACKGROUND OF THE INVENTION

Field of the Invention

The present disclosure relates to a bolus and a method for producing the same.

Description of the Related Art

Utilization of radiations such as X rays, γ rays, electron beams, neutrons, and α rays and laser beams for treatment of diseases such as cancers by irradiating human bodies with these rays has been widespread. Generally, when substances are irradiated with radiations, the original dose of radiations exponentially decreases as the radiations go deep into the substances. However, scattered rays relatively increase in deeper regions and are directionally varied.

Particularly, recoil electrons (scattered rays) due to high-energy radiations are mainly scattered frontward and therefore rarely scattered sidewards. Hence, the maximum dose is obtained at some depth from the surface dose. If a treatment is applied without taking into consideration such a behavior of radiations in skin, normal tissues other than the target (affected part) may be wastefully irradiated with radiations and affected harmfully.

In order to prevent this harm, a bolus formed of a substance equivalent to human tissues is used.

Examples of the material of the bolus proposed up until now include plastic, paraffin, synthetic rubbers, silicone, gum base, agar, acetoacetylated water-soluble polymeric compounds (for example, see Japanese Examined Patent Publication No. 03-26994), nonflowable gel produced by repeating a freezing or thawing operation of a specific polyvinyl alcohol (for example, see Japanese Examined Patent Publication No. 06-47030), a water-containing gel of a specific natural organic polymer (for example, see Japanese Patent No. 2999184), and transparent silicone gel (for example, see Japanese Unexamined Patent Application Publication No. 11-221293).

SUMMARY OF THE INVENTION

According to one aspect of the present disclosure, a bolus is formed of a hydrogel including water, a polymer, and a mineral. The bolus is applied to a patient who receives a radiation therapy.

DESCRIPTION OF THE EMBODIMENTS

The present disclosure has an object to provide a bolus suitable for a radiation therapy and having an excellent handleability.

The present disclosure can provide a bolus suitable for a radiation therapy and having an excellent handleability.

(Bolus)

A bolus of the present disclosure is a bolus to be applied to a patient who receives a radiation therapy.

The bolus is formed of a hydrogel containing water, a polymer, and a mineral, preferably contains at least any one of an organic solvent and a phosphonic acid compound, and further contains other components as needed.

The bolus preferably contains a hydrogel that is formed by the water being contained in a three-dimensional network structure formed by the polymer and the mineral being combined with each other.

<Polymer>

Examples of the polymer include polymers containing an amide group, an amino group, a hydroxyl group, a tetramethyl ammonium group, a silanol group, and an epoxy group. The polymer is preferably water-soluble.

The polymer may be a homopolymer or a heteropolymer (copolymer), may be modified, may have a known functional group introduced, or may be in the form of a salt. The polymer is preferably a homopolymer.

In the present disclosure, water-solubility of the polymer means that, for example, when 1 g of the polymer is mixed and stirred in 100 g of water having a temperature of 30 degrees C., 90% by mass or greater of the polymer dissolves.

The polymer is obtained by polymerizing a polymerizable monomer. The polymerizable monomer will be described in a method for producing a bolus described below.

<Water>

As the water, for example, pure water such as ion-exchanged water, ultrafiltrated water, reverse osmotic water, and distilled water or ultrapure water can be used.

Any other component such as an organic solvent may be dissolved or dispersed in the water with a view to, for example, imparting a moisture retaining property, imparting an antimicrobial activity, imparting conductivity, and adjusting hardness.

<Mineral>

The mineral is not particularly limited and may be appropriately selected depending on the intended purpose. Examples of the mineral include a layered clay mineral.

Figure 1:
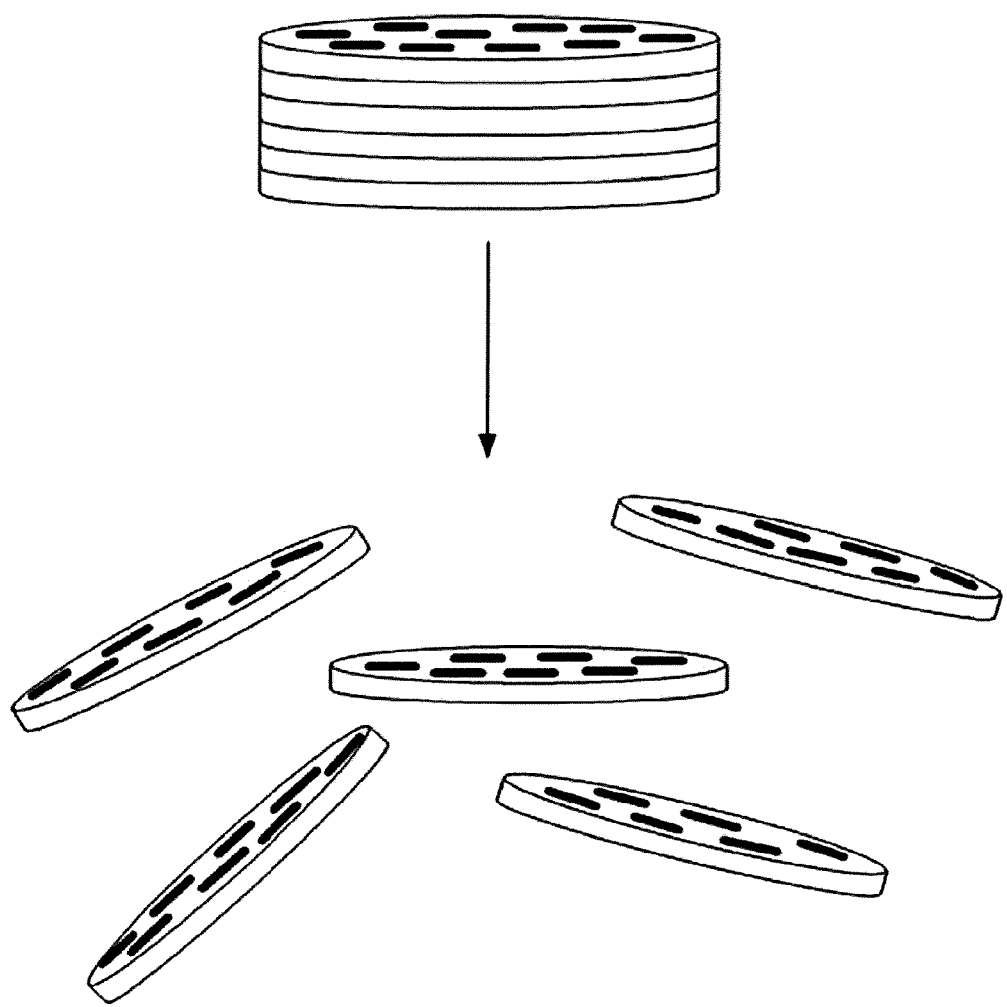
FIG. 1 is an exemplary diagram illustrating a layered clay mineral as a mineral, and an example of a state of the layered clay mineral being dispersed in water.

The layered clay mineral has a state wherein two-dimensional discoid crystals including a unit lattice in the crystals are stacked as illustrated in the upper section of FIG. 1. When the layered clay mineral is dispersed in water, the crystals are separated into single-layer forms to become discoid crystals as illustrated in the lower section of FIG. 1.

Examples of the layered clay mineral include smectite and mica. More specific examples of the layered clay mineral include hectorite containing sodium as an interlayer ion, montmorillonite, saponite, and synthetic mica. One of these layered clay minerals may be used alone or two or more of these layered clay minerals may be used in combination. Among these layered clay minerals, hectorite is preferable because a bolus having a high elasticity can be obtained.

The hectorite may be an appropriately synthesized product or a commercially available product. Examples of the commercially available product include synthetic hectorite (LAPONITE XLG, available from Rock Wood), SWN (available from Coop Chemical Ltd.), and fluorinated hectorite SWF (available from Coop Chemical Ltd.). Among these commercially available products, synthetic hectorite is preferable in terms of the elastic modulus of the bolus.

The content of the mineral is preferably 1% by mass or greater but 40% by mass or less and more preferably 1% by mass or greater but 25% by mass or less relative to the total amount of the bolus in terms of the elastic modulus and hardness of the bolus.

<Organic Solvent>

The organic solvent is contained in order to increase the moisture retaining property of the bolus.

Examples of the organic solvent include: alkyl alcohols containing from 1 through 4 carbon atoms, such as methyl alcohol, ethyl alcohol, n-propyl alcohol, isopropyl alcohol, n-butyl alcohol, sec-butyl alcohol, and tert-butyl alcohol; amides such as dimethyl formamide and dimethyl acetamide; ketones or ketone alcohols such as acetone, methyl ethyl ketone, and diacetone alcohol; ethers such as tetrahydrofuran and dioxane; polyvalent alcohols such as ethylene glycol, propylene glycol, 1,2-propanediol, 1,2-butanediol, 1,3-butanediol, 1,4-butanediol, diethylene glycol, triethylene glycol, 1,2,6-hexanetriol, thioglycol, hexylene glycol, and glycerin; polyalkylene glycols such as polyethylene glycol and polypropylene glycol; lower alcohol ethers of polyvalent alcohols, such as ethylene glycol monomethyl (or ethyl) ether, diethylene glycol methyl (or ethyl) ether, and triethylene glycol monomethyl (or ethyl) ether; alkanol amines such as monoethanol amine, diethanol amine, and triethanol amine; N-methyl-2-pyrrolidone; 2-pyrrolidone; and 1,3-dimethyl-2-imidazolidinone. One of these organic solvents may be used alone or two or more of these organic solvents may be used in combination. Among these organic solvents, polyvalent alcohols are preferable and glycerin and propylene glycol are more preferable in terms of a moisture retaining property.

The content of the organic solvent is preferably 10% by mass or greater but 50% by mass or less relative to the total amount of the bolus. When the content of the organic solvent is 10% by mass or greater, an effect of preventing drying can be sufficiently obtained. When the content of the organic solvent is 50% by mass or less, the layered clay mineral is uniformly dispersed.

When the content of the organic solvent is 10% by mass or greater but 50% by mass or less, a favorable functionality as a bolus can be obtained with a small difference from the body composition.

<Phosphonic Acid Compound>

The phosphonic acid compound is not particularly limited and may be appropriately selected depending on the intended purpose. Examples of the phosphonic acid compound include 1-hydroxyethane-1,1-diphosphonic acid.

<Other Components>

The other components are not particularly limited and may be appropriately selected depending on the intended purpose. Examples of the other components include a stabilizing agent, a surface treating agent, a polymerization initiator, a colorant, a viscosity modifier, a tackifier, an antioxidant, an age resistor, a cross-linking promoter, an ultraviolet absorber, a plasticizer, an antiseptic, and a dispersant.

<Coating Film>

It is effective to provide a coating film over the surface of the bolus for the following three purposes.

(1) To maintain the shape of the bolus (2) To improve the storage stability (drought resistance and antiseptic property) of the bolus (3) To improve the appearance of the bolus.

In order to maintain the shape of the bolus, it is preferable to impart an elastic force to the coating film for preventing collapse of the bolus due to the deadweight. It is preferable that a difference in Young's modulus of the bolus due to presence and absence of the coating film be 0.01 MPa or greater.

The material forming the coating film is not particularly limited and may be appropriately selected depending on the intended purpose. Examples of the material include polyester, polyolefin, polyethylene terephthalate, polyphenylene sulfide (PPS), polypropylene, polyvinyl alcohol (PVA), polyethylene, polyvinyl chloride, cellophane, acetate, polystyrene, polycarbonate, nylon, polyimide, fluororesins, and paraffin waxes. One of these materials may be used alone or two or more of these materials may be used in combination. As the material forming the coating film, a commercially available product may be used. Examples of the commercially available product include PLASTICOAT #100 (available from Daikyo Chemical Co., Ltd.).

The film thickness of the coating film is not particularly limited, may be appropriately selected depending on the intended purpose, and is preferably 100 micrometers or less and more preferably 10 micrometers or greater but 50 micrometers or less. When the film thickness of the coating film is 100 micrometers or less, the texture of the hydrogel constituting the bolus can be maintained.

It is possible to improve the appearance of the bolus by forming the coating film over the surface of the bolus. For example, when the surface of the bolus has a scar or a surface roughness, the coating film can make up for the appearance. Moreover, the internal bolus can be protected when the coating film over the surface serves as a sacrificial layer.

Furthermore, because the surface of the bolus does not accept writing such as marking, the coating film formed over the surface of the bolus can add to the functionality as the bolus, allowing, for example, the procedure of a radiation therapy and the name of the patient to be written.

The method for forming the coating film is not particularly limited and may be appropriately selected depending on the intended purpose. Examples of the method include a method of dissolving the material for forming the coating film in a solvent and coating the resultant over the surface of the bolus. Examples of the coating method include a brush, spray, and dip coating.

Examples of the method also include a method of using a heat-shrinkable film as the material for forming the coating film and laminating the heat-shrinkable film over the surface of the hydrogel structure.

Moreover, it is also possible to dissolve the material for forming the coating film in a solvent and simultaneously form the coating film when producing the bolus using a three-dimensional printer and a liquid material for producing a bolus.

In any case, what matters is close adhesiveness with skin. Therefore, what matters is to form a coating film that would not spoil the surface profile of the bolus produced based on three-dimensional data of a body surface, which is the target of radiation irradiation, of an individual treatment recipient.

In order to improve the storage stability of the bolus, there is a need for improving the drought resistance and the antiseptic property.

In order to improve the drought resistance, it is effective to suppress the water vapor permeability and the oxygen permeability of the coating film. Specifically, the water vapor permeability (JIS K7129) is preferably 500 $g/m^2 \cdot d$ or lower. The oxygen permeability (JIS Z1702) is preferably 100,000 $cc/m^2/hr/atm$ or lower.

In order to improve the antiseptic property, it is preferable to add an antiseptic in the coating film. The antiseptic is not particularly limited and may be appropriately selected depending on the intended purpose. Examples of the antiseptic include dehydroacetate, sorbate, benzoate, pentachlorophenol sodium, 2-pyridinethiol-1-oxide sodium, 2,4-dimethyl-6-acetoxy-m-dioxane, and 1,2-benzthiazolin-3-one.

Generally, it is preferable that a bolus that is worth practical use satisfy such properties and functionalities as (1) being formed of a substance equivalent to human tissues, (2) being homogeneous, (3) having an excellent plasticity and an appropriate elasticity to have a good shape conformity to and a good close adhesiveness with a living body, (4) being nontoxic, (5) not undergoing energy variation, (6) having a uniform thickness, (7) being free of air inclusion, (8) having a high transparency, and (9) being easily disinfectable.

The bolus of the present disclosure is a bolus to be applied to a patient who receives a radiation therapy. It is preferable that the bolus have a shape conforming to a body surface, which is the target of radiation irradiation, of a patient.

Here, having a shape conforming to a body surface means having a certain shape that is convex or concave with respect to a concave portion or a convex portion of the body of the patient, the concave portion or the convex portion being included in a body surface, which is the target of radiation irradiation. This makes it possible to produce a bolus that snugly fits the skin of the patient.

The bolus of the present disclosure is a bolus to be applied to a patient who receives a radiation therapy. It is preferable that the bolus have a radiation transmittance distribution matching the affected part of the patient.

Here, an advantage obtained when the bolus has a radiation transmittance distribution will be described. For example, there are the following disadvantages in an X-ray irradiation therapy.

Body surface portions other than cancer cells are affected by radiations more than the cancer cells, and cells behind the cancer cells are also affected.

Shape processing is unavailable.

There is a need for applying irradiation while avoiding organs that are lethal if a trouble occurs, such as a heart and a lung.

Figure 2:
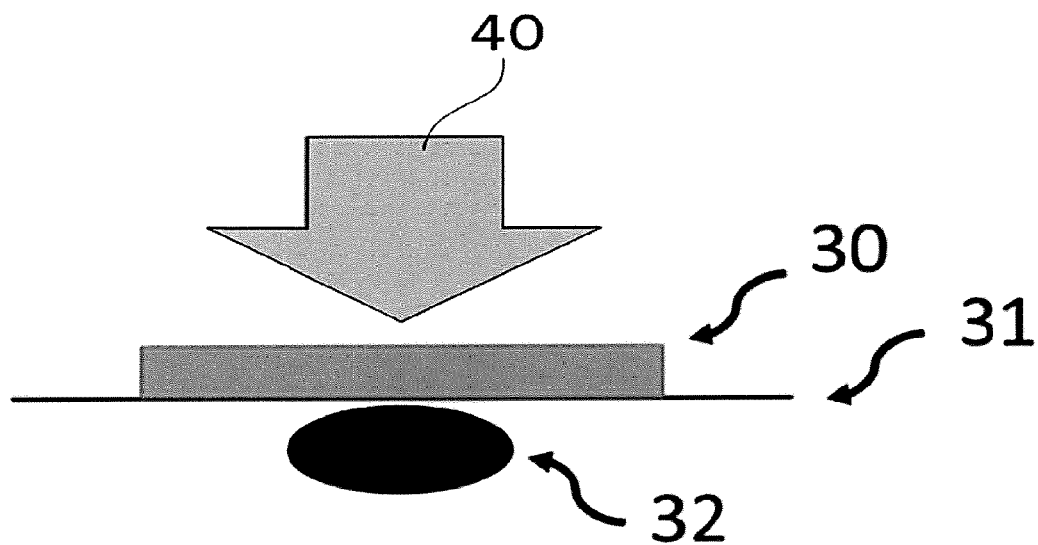
FIG. 2 is a concept diagram of irradiation of an affected part of a patient with an X ray using a bolus.

Here, FIG. 2 is a schematic diagram illustrating irradiation of an affected part 32 of a patient with an X ray 40. With a bolus 30 disposed on a skin surface 31 of the affected part 32, the X-ray 40 is applied through the surface of the bolus.

Figure 3:
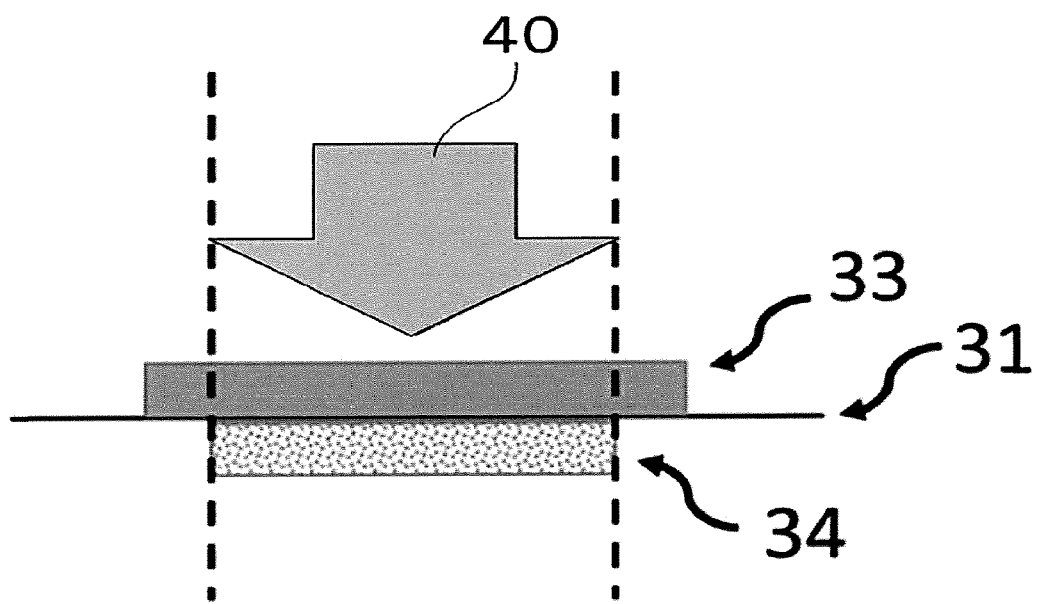
FIG. 3 is a diagram of a case where X-ray irradiation is performed using a homogeneous bolus.

When an existing bolus 33 is used as illustrated in FIG. 3, the bolus 33, which has a homogeneous composition, can control the irradiation depth of an X-ray, but in a uniform controlling manner. Therefore, the controlling only functions in a manner to make the peak of the incident X-ray 40 uniform in the depth direction and over the peripheral area. This point is related with the unavailability of shape processing mentioned above. Therefore, cells and body surface portions other than cancer cells are strongly affected by the radiation (X-ray). Note that the reference sign 34 in FIG. 3 denotes the X-ray (homogeneous) that has passed through the bolus.

Figure 4:
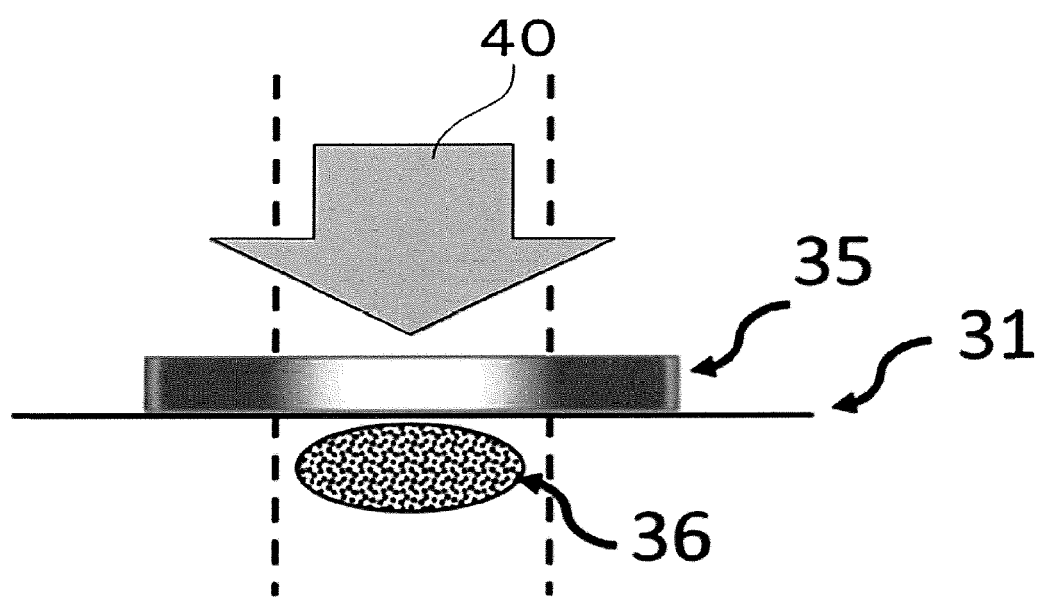
FIG. 4 is a diagram of a case where X-ray irradiation is performed using a bolus having a composition distribution.

As compared, FIG. 4 illustrates a case where an X-ray transmittance distribution is imparted to a bolus. In this case, a bolus 35 has a composition variation to have a composition distribution. This makes it possible to vary the X-ray transmittance and impart an X-ray transmittance distribution. FIG. 4 illustrates a case where the thickness is constant and only the composition is varied. However, the film thickness may also be varied at the same time. Combining both enables irradiation of the X-ray 40 focused on the cancer cells. This makes it possible to suppress any other portions than the cancer cells from being adversely affected. The reference sign 36 in FIG. 4 illustrates the X-ray (with a distribution) that has passed through the bolus.

There are two ways of forming an X-ray transmittance distribution, namely, imparting a composition distribution to the bolus and controlling the distribution based on the shape as described below. Alternatively, both may be combined.

—Composition Distribution—

As described above, in order to form an X-ray transmittance distribution in the bolus, there is a method of imparting a distribution in the composition constituting the bolus.

Figure 5:
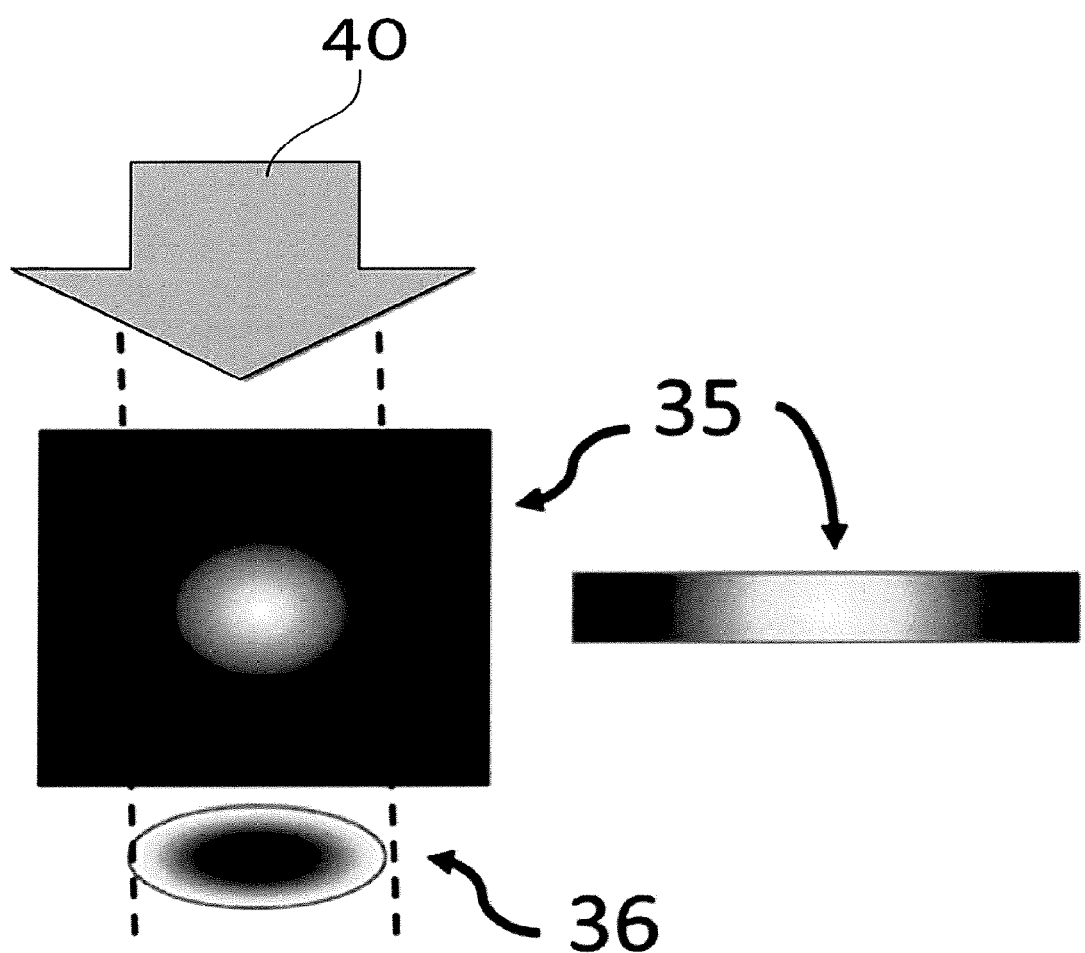
FIG. 5 is a concept diagram of a top view of a bolus having a composition distribution and an amount of X-ray transmission.

FIG. 5 is a diagram of a top view of a bolus 35 having a composition distribution and a transmittance distribution of an X-ray 40. The black portion of the bolus is where there is a composition with a high attenuance of the X-ray 40, and the white portion is a portion with a high transmittance. The X-ray 40 that has passed through such a bolus has a high intensity in the center and can irradiate, for example, the cancer cells in a focused manner.

As the method for forming a composition distribution, use of a three-dimensional printer of an inkjet type and a plurality of liquid materials for producing a bolus makes it possible to form a composition distribution. Particularly, the hydrogel used in the present disclosure can have a unique relationship between the composition (water content) and the X-ray transmittance, allowing easy transmittance control.

—Shape Control—

In order to impart an X-ray transmittance distribution, a method based on shape control is also available.

Figure 6:
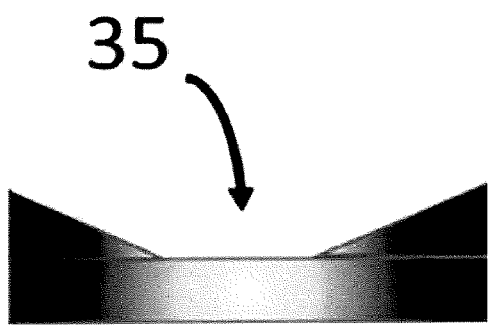
FIG. 6 is a concept diagram of a shape change of a bolus.

For example, a shape illustrated in FIG. 6 can suppress the dosage to the peripheral regions of the cancer cells.

As can be understood, a bolus composition distribution, arbitrary control of the film thickness, and combination of both are unavailable with existing crafting techniques (object production with a die). These kinds of epoch-making means can be conceived with an object producing method using a three-dimensional printer.

For example, the shape, size, and structure of the bolus are not particularly limited and may be appropriately selected depending on the intended purpose.

Examples of the bolus include a flat-plate-shaped bolus. In order to closely attach the bolus to the surface of a human body, the flat-plate-shaped bolus is used by being pressed onto the skin or by being cut into pieces having an appropriate size to join the pieces together.

The bolus of the present disclosure is practically usable when the CT value (HU) of the bolus measured by a computer tomography method is in a range of −100 or higher but 100 or lower, preferably 0 or higher but 100 or lower, and more preferably 0 or higher but 70 or lower.

The CT value is a value obtained by a computer tomography device based on calibrations that a value 1,000 is assigned for a bone, a value 0 is assigned for water, and a value −1,000 is assigned for the air.

The bolus of the present disclosure is used for a radiation therapy and desired to be close to the body composition. Here, the body composition cannot be flatly defined, and has different CT values from a body portion to a body portion. A muscle has a CT value of about from 35 through 50. Internal organs also have different CT values from a body portion to a body portion, and it is known that a liver has a CT value of about from 45 through 75 and a pancreas has a CT value of about from 25 through 55. A fat has a CT value of about from −50 through −100 and blood has a CT value of about from 10 through 30.

Therefore, a bolus having the CT value of roughly −100 or higher but 100 or lower can have substantially the same characteristic as a human tissue in terms of absorption or scattering of radiation, although depending on the body portion to be irradiated with radiation. When the CT value is in a more preferable range of 0 or higher but 100 or lower or in a yet more preferable range of 0 or higher but 70 or lower, the bolus can be said to have a very close characteristic.

Because the hydrogel used in the present disclosure is formed of a polymer and water as the main components, the hydrogel has a close composition to a human body in the first place and has a close CT value to the CT value of a human body.

Moreover, it is possible to arbitrarily change the composition ratio between the materials constituting the hydrogel (the abundance ratios of the polymer and the mineral relative to water or the mixing ratio between water and the organic solvent) to some degree. This can bring about a change in the CT value, thus making it possible to control the CT value to some degree in a manner to match the portion to be treated with a radiation therapy.

As described above, a bolus formed of the hydrogel satisfies all physical properties and characteristics needed to qualify as a bolus. The hydrogel can be raised as one of the optimum materials as the material for constituting a bolus.

(Method for Producing Bolus)

A method for producing a bolus of the present disclosure includes producing a bolus using a liquid material for producing a bolus, the liquid material containing water, a mineral, and a polymerizable monomer.

<Liquid Material for Producing Bolus>

The liquid material for producing a bolus contains water, a mineral, and a polymerizable monomer, preferably contains at least any one of an organic solvent and a phosphonic acid compound, and further contains other components as needed.

As the water, the mineral, the organic solvent, the phosphonic acid compound, and the other components, the same substances as the substances used in the bolus can be used.

—Polymerizable Monomer—

The polymerizable monomer is a compound that contains one or more unsaturated carbon-carbon bonds. Examples of the polymerizable monomer include monofunctional monomers and multifunctional monomers. Examples of the multifunctional monomers include bifunctional monomers, trifunctional monomers, and tetrafunctional or higher monomers.

The monofunctional monomer is a compound containing one unsaturated carbon-carbon bond. Examples of the monofunctional monomer include acrylamide, N-substituted acrylamide derivatives, N,N-disubstituted acrylamide derivatives, N-substituted methacrylamide derivatives, N,N-disubstituted methacrylamide derivatives, and other monofunctional monomers. One of these monofunctional monomers may be used alone or two or more of these monofunctional monomers may be used in combination.

Examples of the N-substituted acrylamide derivatives, the N,N-disubstituted acrylamide derivatives, the N-substituted methacrylamide derivatives, or the N,N-disubstituted methacrylamide derivatives include N,N-dimethylacrylamide (DMAA) and N-isopropylacrylamide.

Examples of the other monofunctional monomers include 2-ethylhexyl (meth)acrylate (EHA), 2-hydroxyethyl (meth)acrylate (HEA), 2-hydroxypropyl (meth)acrylate (HPA), acryloylmorpholine (ACMO), caprolactone-modified tetrahydrofurfuryl (meth)acrylate, isobornyl (meth)acrylate, 3-methoxybutyl (meth)acrylate, tetrahydrofurfuryl (meth)acrylate, lauryl (meth)acrylate, 2-phenoxyethyl (meth)acrylate, isodecyl (meth)acrylate, isooctyl (meth)acrylate, tridecyl (meth)acrylate, caprolactone (meth)acrylate, ethoxylated nonylphenol (meth)acrylate, and urethane (meth)acrylate. One of these monofunctional monomers may be used alone or two or more of these monofunctional monomers may be used in combination.

When the monofunctional monomer is polymerized, a water-soluble organic polymer containing, for example, an amide group, an amino group, a hydroxyl group, a tetramethyl ammonium group, a silanol group, or an epoxy group is obtained.

The water-soluble organic polymer containing, for example, an amide group, an amino group, a hydroxyl group, a tetramethyl ammonium group, a silanol group, or an epoxy group is a constituent component advantageous for maintaining the strength of the bolus.

The content of the monofunctional monomer is not particularly limited, may be appropriately selected depending on the intended purpose, and is preferably 1% by mass or greater but 10% by mass or less and more preferably 1% by mass or greater but 5% by mass or less relative to the total amount of the liquid material for producing a bolus. When the content of the monofunctional monomer is in the range of 1% by mass or greater but 10% by mass or less, there are advantages that the dispersion stability of a layered clay mineral in the liquid material for producing a bolus is maintained, and that the elongatability of the bolus is improved. The elongatability refers to a property of the bolus of elongating when drawn and not being torn.

Examples of the bifunctional monomer include tripropylene glycol di(meth)acrylate, triethylene glycol di(meth)acrylate, tetraethylene glycol di(meth)acrylate, polypropylene glycol di(meth)acrylate, neopentyl glycol hydroxypivalic acid ester di(meth)acrylate (MANDA), hydroxypivalic acid neopentyl glycol ester di(meth)acrylate (HPNDA), 1,3-butanediol di(meth)acrylate (BGDA), 1,4-butanediol di(meth)acrylate (BUDA), 1,6-hexanediol di(meth)acrylate (HDDA), 1,9-nonanediol di(meth)acrylate, diethylene glycol di(meth)acrylate (DEGDA), neopentyl glycol di(meth)acrylate (NPGDA), tripropylene glycol di(meth)acrylate (TPGDA), caprolactone-modified hydroxypivalic acid neopentyl glycol ester di(meth)acrylate, propoxylated neopentyl glycol di(meth)acrylate, ethoxy-modified bisphenol A di(meth)acrylate, polyethylene glycol 200 di(meth)acrylate, polyethylene glycol 400 di(meth)acrylate, and methylene bisacrylamide. One of these bifunctional monomers may be used alone or two or more of these bifunctional monomers may be used in combination.

Examples of the trifunctional monomer include trimethylolpropane tri(meth)acrylate (TMPTA), pentaerythritol tri(meth)acrylate (PETA), triallyl isocyanate, tris(2-hydroxyethyl)isocyanurate tri(meth)acrylate, ethoxylated trimethylolpropane tri(meth)acrylate, propoxylated trimethylolpropane tri(meth)acrylate, and propoxylated glyceryl tri(meth)acrylate. One of these trifunctional monomers may be used alone or two or more of these trifunctional monomers may be used in combination.

Examples of the tetrafunctional or higher monomer include pentaerythritol tetra(meth)acrylate, ditrimethylolpropane tetra(meth)acrylate, dipentaerythritol hydroxy penta(meth)acrylate, ethoxylated pentaerythritol tetra(meth)acrylate, penta(meth)acrylate ester, and dipentaerythritol hexa(meth)acrylate (DPHA). One of these tetrafunctional or higher monomers may be used alone or two or more of these tetrafunctional or higher monomers may be used in combination.

The content of the multifunctional monomer is preferably 0.001% by mass or greater but 1% by mass or less and more preferably 0.01 by mass or greater but 0.5% by mass or less relative to the total amount of the liquid material for producing a bolus. When the content of the multifunctional monomer is 0.001% by mass or greater but 1% by mass or less, the elastic modulus and hardness of the bolus to be obtained can be adjusted to be within appropriate ranges.

It is preferable to cure the liquid material for producing a bolus by using a polymerization initiator. The polymerization initiator is used by being added in the liquid material for producing a bolus.

—Polymerization Initiator—

Examples of the polymerization initiator include a thermal polymerization initiator and a photopolymerization initiator.

The thermal polymerization initiator is not particularly limited and may be appropriately selected depending on the intended purpose. Examples of the thermal polymerization initiator include azo-based initiators, peroxide initiators, persulfate initiators, and redox (oxidoreduction) initiators.

Examples of the azo-based initiators include VA-044, VA-46B, V-50, VA-057, VA-061, VA-067, VA-086, 2,2'-azobis(4-methoxy-2,4-dimethylvaleronitrile) (VAZO 33), 2,2'-azobis(2-amidinopropane)dihydrochloride (VAZO 50), 2,2'-azobis(2,4-dimethylvaleronitrile) (VAZO 52), 2,2'-azobis(isobutyronitrile) (VAZO 64), 2,2'-azobis-2-methylbutyronitirle (VAZO 67), and 1,1-azobis(1-cyclohexanecarbonitrile) (VAZO 88) (all available from DuPont Chemicals Company), 2,2'-azobis(2-cyclopropylpropionitrile) and 2,2'-azobis(methylisobutyrate) (V-601) (available from Wako Pure Chemical Industries, Ltd.).

Examples of the peroxide initiators include benzoyl peroxide, acetyl peroxide, lauroyl peroxide, decanoyl peroxide, dicetyl peroxydicarbonate, di(4-t-butylcyclohexyl)peroxydicarbonate (PERKADOX 16S) (available from Akzo Nobel), di(2-ethylhexyl) peroxydicarbonate, t-butyl peroxypivalate (LUPERSOL 11) (available from Elf Atochem), t-butyl peroxy-2-ethyl hexanoate (TRIGONOX 21-050) (available from Akzo Nobel), and dicumyl peroxide.

Examples of the persulfate initiators include potassium persulfate, sodium persulfate, ammonium persulfate, and sodium peroxodisulfate.

Examples of the redox (oxidoreduction) initiators include a combination of the persulfate initiator with a reducing agent such as sodium hydrogen metasulfite and sodium hydrogen sulfite, a system based on the organic peroxide and tertiary amine (for example, a system based on benzoyl peroxide and dimethyl aniline), and a system based on organic hydroperoxide and a transition metal (for example, a system based on cumene hydroperoxide and cobalt naphthenate).

As the photopolymerization initiator, an arbitrary substance that produces radicals in response to irradiation of light (particularly, an ultraviolet ray having a wavelength of from 220 nm through 400 nm) can be used.

Examples of the photopolymerization initiator include acetophenone, 2,2-diethoxyacetophenone, p-dimethyl aminoacetophenone, benzophenone, 2-chlorobenzophenone, p,p'-dichlorobenzophenone, p,p-bisdiethyl aminobenzophenone, Michler's ketone, benzyl, benzoin, benzoin methyl ether, benzoin ethyl ether, benzoin isopropyl ether, benzoin-n-propyl ether, benzoin isobutyl ether, benzoin-n-butyl ether, benzyl methyl ketal, thioxanthone, 2-chlorothioxanthone, 2-hydroxy-2-methyl-1-phenyl-1-one, 1-(4-isopropylphenyl)2-hydroxy-2-methylpropan-1-one, methylbenzoyl formate, 1-hydroxycyclohexylphenyl ketone, azobis isobutyronitrile, benzoyl peroxide, and di-tert-butyl peroxide. One of these photopolymerization initiators may be used alone or two or more of these photopolymerization initiators may be used in combination.

Tetramethyl ethylenediamine is used as an initiator for a polymerization/gelation reaction that transforms acrylamide into polyacrylamide gel.

The method for producing a bolus of the present disclosure is roughly classified into two kinds, including a method of producing a bolus using a die and a method of directly producing a bolus using a three-dimensional printer.

<Producing Method Using Die>

The method of producing a bolus using a die is a method of pouring the liquid material for producing a bolus into a die and curing the liquid material.

It is preferable to secure the die to the surface of the skin of a body portion, which is to be treated, of a treatment recipient, pour the liquid material for producing a bolus into the die, and cure the liquid material. This enables production of a bolus having a shape conforming to the body surface (the body portion to be treated; affected part), which is the target of radiation irradiation, of the treatment recipient.

In order to produce a bolus having a desired shape, a die having the intended shape is prepared. Examples of the die include a quadrangular die 110 as illustrated in FIG. 7 and an annular die 112 illustrated in FIG. 8.

Figure 7:
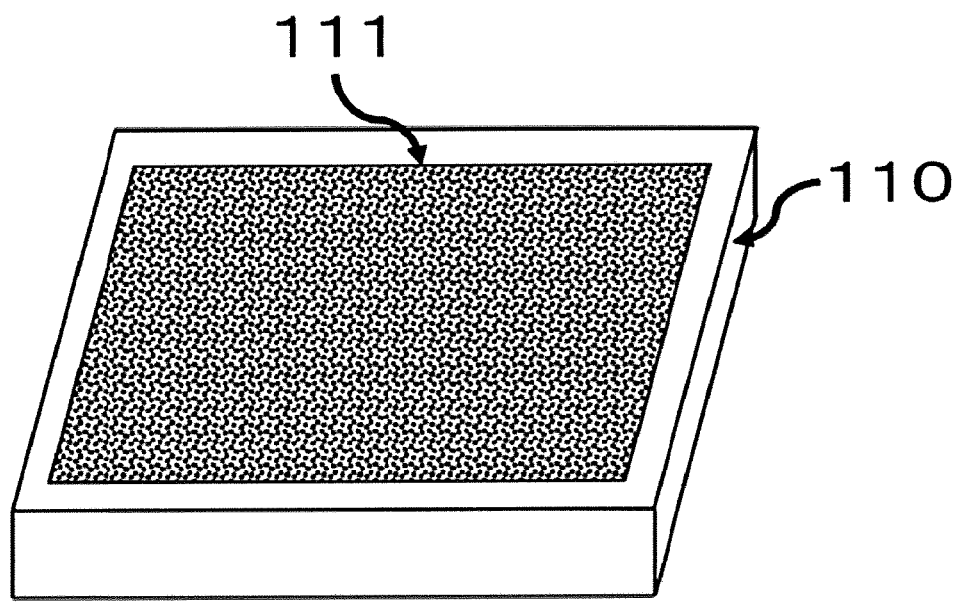
FIG. 7 is a schematic diagram illustrating an example of a die used for molding a bolus of the present disclosure.
Figure 8:
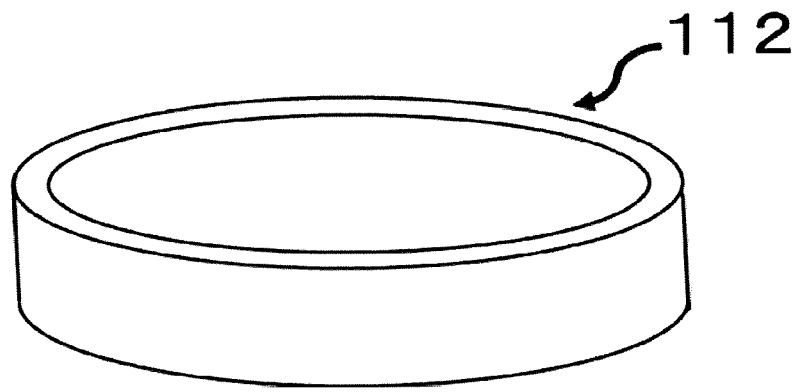
FIG. 8 is a schematic diagram illustrating another example of a die used for molding a bolus of the present disclosure.

The liquid material for producing a bolus is injected into the quadrangular die 110 illustrated in FIG. 7.

In the case of using a thermal polymerization initiator for curing, the reaction temperature is controlled depending on the kind of the initiator. The liquid material for producing a bolus is injected, sealed for air (oxygen) shutoff, and then heated to room temperature or a predetermined temperature to be allowed to undergo a polymerization reaction.

Figure 9:
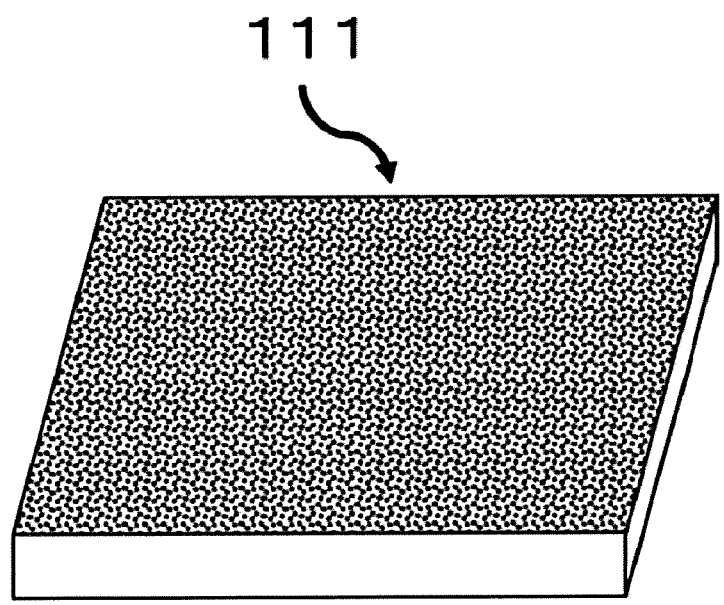
FIG. 9 is a schematic diagram illustrating an example of a bolus of the present disclosure.

After polymerization is completed, a bolus 111 is taken out from the quadrangular die 110. In this way, the bolus 111 illustrated in FIG. 9 is produced.

In the case of using a photopolymerization initiator for curing, there is a need for irradiating the liquid material for producing a bolus with an energy ray such as an ultraviolet ray, as a curing method. Therefore, the die to be used is formed of a material transparent to the energy ray. The liquid material is injected into such a die, sealed for air (oxygen) shutoff, and then irradiated with an energy ray from outside the die. After polymerization is completed in this way, the bolus is taken out from the die. In this way, the bolus is produced.

It is preferable to produce the die using a three-dimensional printer.

The type of the three-dimensional printer is not particularly limited. However, it is preferable to produce the die using a material or a type that would not allow leakage of the liquid material for producing a bolus, because the liquid material for forming a bolus is injected into the die for curing. For example, an inkjet (material jet) type, a stereolithography type, and a laser sintering type can be suitably used.

It is preferable to produce a bolus by pouring the liquid material for producing a bolus into a die, which is produced using a three-dimensional printer based on shape data of a skin surface of a patient, and curing the liquid material.

Here, having a shape conforming to the body surface means having a certain shape that is convex or concave with respect to a concave portion or a convex portion of the body of a treatment recipient, the concave portion or the convex portion being included in a body surface, which is the target of radiation irradiation, of the treatment recipient. This makes it possible to produce a bolus that snugly fits the skin of the treatment recipient.

Figure 11:
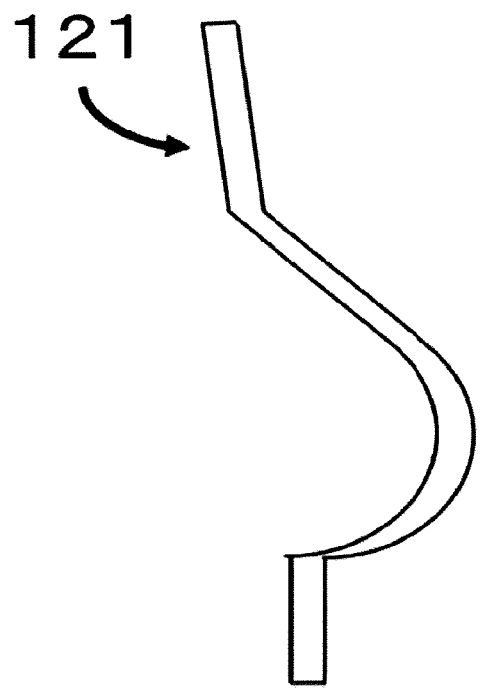
FIG. 11 is a schematic diagram of a male die for a bolus for a breast produced using a three-dimensional printer.
Figure 12:
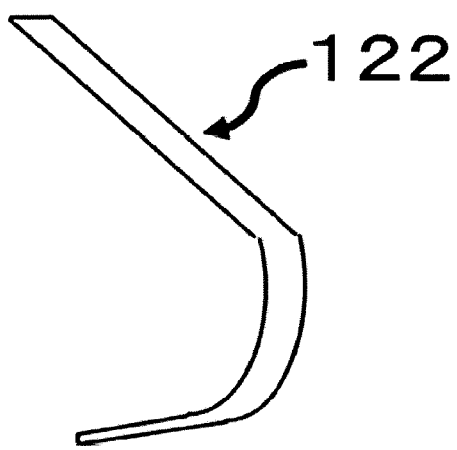
FIG. 12 is a schematic diagram of a female die for a bolus for a breast produced using a three-dimensional printer.
Figure 13:
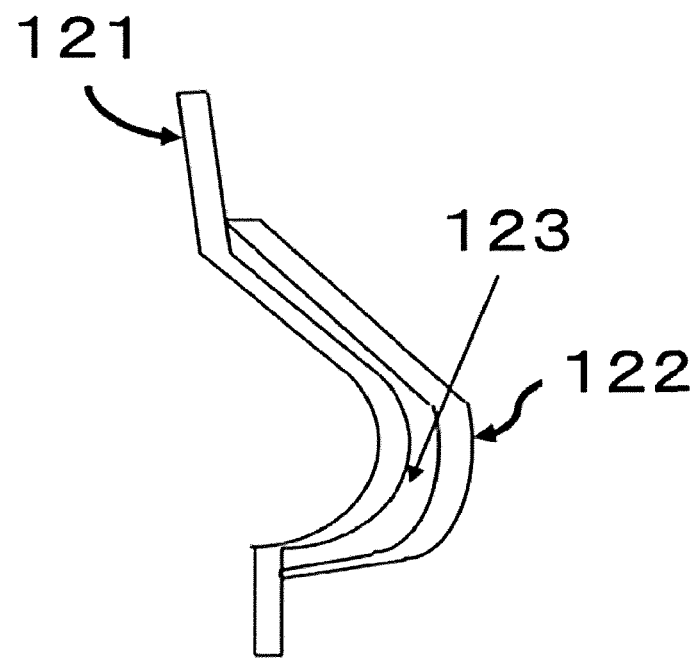
FIG. 13 is a schematic diagram illustrating a combined state of boluses for a breast produced using a three-dimensional printer.
Figure 14:
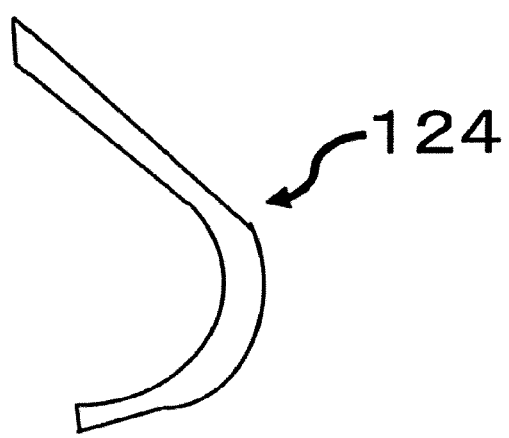
FIG. 14 is a schematic diagram of a bolus taken out from dies.

For example, in the case of producing a die conforming to a breast shape, CT data of a breast of a treatment recipient (patient) is acquired and converted into three-dimensional (3D) data in order that male and female dies can be produced based on the data. Based on the three-dimensional (3D) data, a male die 121 for producing a three-dimensional bolus for the breast of the patient illustrated in FIG. 11 is produced using a three-dimensional printer. Based on the patient's personal data, a female die 122 for producing a three-dimensional bolus for the breast illustrated in FIG. 12 is produced using a three-dimensional printer. When the produced male die 121 and female die 122 are combined with each other as illustrated in FIG. 13, a gap 123 is formed between both of the dies. By injecting the liquid material for producing a bolus of the present disclosure into this gap 123 and curing the liquid material, it is possible to produce a three-dimensional bolus 124 for a breast illustrated in FIG. 14.

<Direct Producing Method Using Three-Dimensional Printer>

Object production using the three-dimensional printer is intended for directly producing an object using a three-dimensional printer and the liquid material for producing a bolus.

It is preferable that the three-dimensional printer be a three-dimensional printer of an inkjet type or a three-dimensional printer of a stereolithography type. Use of these types enables a composition distribution or shape control that is suited to the condition of a body portion to be treated, of a patient, and enables production of a bolus having a radiation transmittance distribution.

For example, it is possible not only to impart a shape conforming to a body surface that is the target of radiation irradiation, using the personal data of a treatment recipient (patient), but also to impart a radiation transmittance distribution as needed.

Also in this case, production is based on personal data of the patient.

For example, in the case of producing a die suited to a breast shape, CT data of a breast is acquired and converted into three-dimensional (3D) data in order that male and female dies can be produced based on the data. Based on the 3D data, a bolus is directly produced using a three-dimensional printer.

It is preferable that the three-dimensional printer be of a type that can print the material of the bolus. It is effective to use a system that is configured to discharge an ink by an inkjet (material jet) method or a dispenser method and cure the ink with UV light. This method allows use of a plurality of materials for producing a bolus, making it possible to impart a distribution in the composition, instead of a uniform composition throughout the bolus. Particularly, it is possible to impart a composition distribution that enables the X-ray transmittance to be controlled to match the affected part of a patient to be treated. This is an effective method in that, for example, normal cells other than cancer cells can be as much as possible protected from being damaged.

Figure 15:
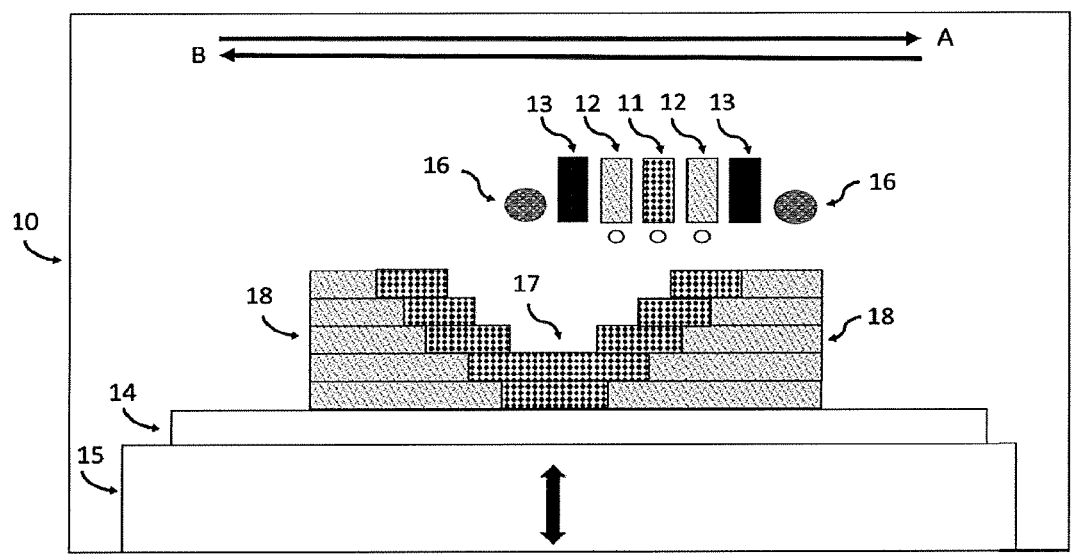
FIG. 15 is a schematic diagram of a three-dimensional printer configured to produce a bolus.

For example, a three-dimensional printer 10 of an inkjet (IJ) type as illustrated in FIG. 15 is configured to use a head unit in which inkjet heads are arranged, and laminate layers by discharging the liquid material for producing a bolus from a liquid material discharging head unit 11 for an object, discharging a support forming liquid material from liquid material discharging head units 12 and 12 for a support, and curing the liquid material for producing a bolus and the support forming liquid material with adjoining ultraviolet ray irradiators 13 and 13.

In order to maintain the liquid material discharging head units 11 and 12 and the ultraviolet ray irradiators 13 at a constant gap from an object (bolus) 17 and a support 18, layer lamination is performed while a stage 15 is lifted down in accordance with the number of times of layer lamination.

In the three-dimensional printer 10, the ultraviolet ray irradiators 13 and 13 are used in moving in the directions of both of the arrows A and B. The surface of a laminated layer of the support forming liquid material is smoothed by the heat generated along with the ultraviolet ray irradiation. As a result, the dimensional stability of the bolus is improved.

Figure 16:
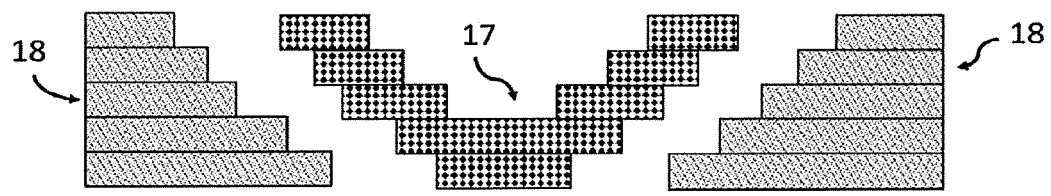
FIG. 16 is a schematic diagram of a state of a bolus produced using a three-dimensional printer being detached from a support material.

After object production is completed, the bolus 17 and the support 18 are pulled in the horizontal direction and detached from each other as illustrated in FIG. 16. As a result, the support 18 is detached as an integral body, and the bolus 17 can be easily taken out.

Figure 17:
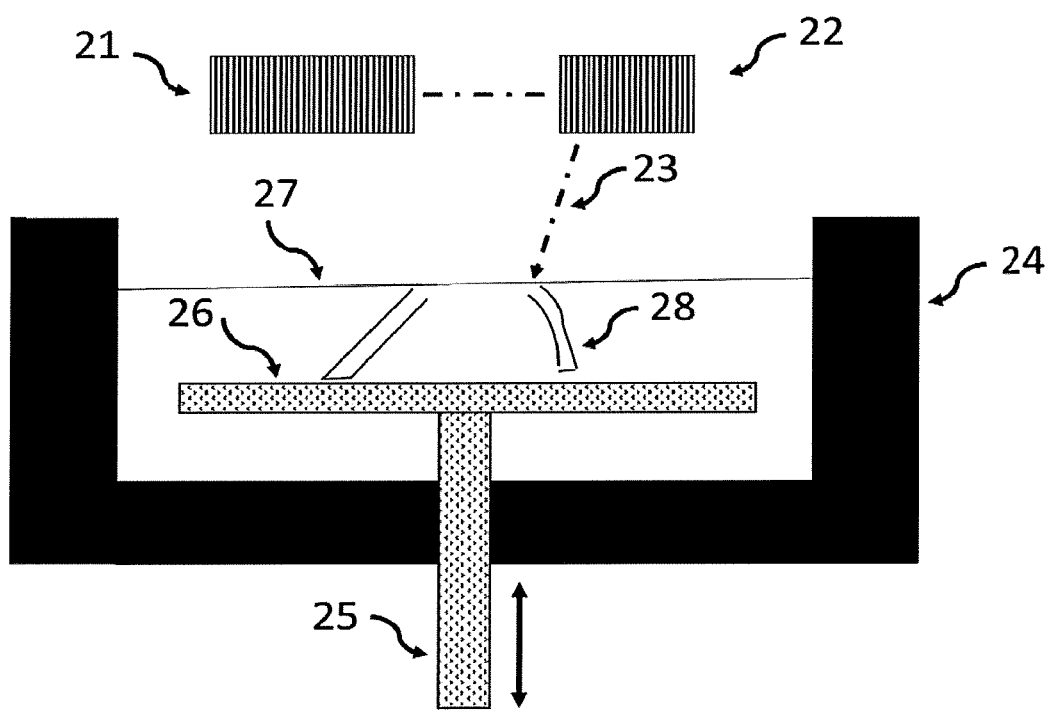
FIG. 17 is a schematic diagram of a three-dimensional printer of another type configured to produce a bolus.

Further, as illustrated in FIG. 17, a three-dimensional printer of a stereolithography type is configured to store the liquid material for producing a bolus in a liquid tank 24, irradiate a surface 27 of the liquid tank 24 with ultraviolet laser light 23 emitted from a laser light source 21 through a laser scanner 22, and produce a cured product on an object production stage 26. The object production stage 26 is lifted down by means of a piston 25. Through repetition of this sequence, a bolus is obtained.

EXAMPLES

The present disclosure will be described below by way of Examples. The present disclosure should not be construed as being limited to these Examples.

Example 1

<Production of Bolus>
—Preparation of Liquid Material for Producing Bolus—

First, to pure water (400 parts by mass) under stirring, synthetic hectorite (LAPONITE XLG, available from Rock Wood) having a composition $[Mg_{5.34}Li_{0.66}Si_8O_{20}(OH)_4]Na^-_{0.66}$ (30 parts by mass) was added little by little as a mineral, and then 1-hydroxyethane-1,1-diphosphonic acid (1.6 parts by mass) was further added, followed by stirring, to prepare a dispersion liquid.

Next, to the obtained dispersion liquid, N,N-dimethylacrylamide (available from Wako Pure Chemical Industries, Ltd.) (40 parts by mass) having been passed through an activated alumina column for removal of a polymerization inhibitor and LIGHT ACRYLATE 9EG-A (available from Kyoeisha Chemical Co., Ltd.) (2 parts by mass) were added as polymerizable monomers.

Next, to the resultant under cooling in an ice bath, a 2% by mass aqueous solution (30 parts by mass) of sodium peroxodisulfate (available from Wako Pure Chemical Industries, Ltd.) in pure water was added, and tetramethyl ethylenediamine (available from Wako Pure Chemical Industries, Ltd.) (2 parts by mass) was further added, followed by stirring and mixing, and then vacuum degassing for 10 minutes. Subsequently, the resultant was subjected to filtration to remove, for example, impurities, to obtain a homogeneous liquid material for producing a bolus.
—Production of Bolus—

The obtained liquid material for producing a bolus was poured into the quadrangular die 110 illustrated in FIG. 7, capped for sealing, and subjected to curing reaction at room temperature (25 degrees C.) for 6 hours. After curing, the resultant was taken out from the quadrangular die 110 and washed with water, to obtain a bolus 111 having a vertical dimension of 200 mm, a horizontal dimension of 200 mm, and a thickness of 10 mm as illustrated in FIG. 9.

Example 2

—Production of Bolus—
A bolus was produced in the same manner as in Example 1, except that 100 parts by mass out of 400 parts by mass of pure water was changed to glycerin, unlike in Example 1.

Example 3

—Production of Bolus—
A bolus was produced in the same manner as in Example 1, except that 100 parts by mass out of 400 parts by mass of pure water was changed to propylene glycol, unlike in Example 1.

Example 4

—Production of Bolus—
A bolus was produced in the same manner as in Example 2, except that 20 parts by mass out of 40 parts by mass of N,N-dimethylacrylamide serving as a polymerizable monomer was changed to acryloylmorpholine, unlike in Example 2.

Example 5

—Production of Bolus—
A bolus was produced in the same manner as in Example 4, except that the amount of synthetic hectorite (LAPONITE XLG, available from Rock Wood) added was changed from 30 parts by mass to 20 parts by mass, unlike in Example 4.

Example 6

—Production of Bolus—
PLASTICOAT #100 (available from Daikyo Chemical Co., Ltd.) was coated over the surface of the bolus produced in Example 1 by a dip coating method, to form a coating film having an average thickness of 30 micrometers.

Example 7

—Production of Bolus—
Polyvinyl alcohol (POVAL 205, available from Kuraray Co., Ltd.) was coated over the surface of the bolus produced in Example 1 by a clip coating method, to form a coating film having an average thickness of 30 micrometers.
<Evaluation>

The following test items of the boluses produced in Examples 1 to 7 were evaluated in order to confirm whether the boluses satisfied all of the properties and conditions needed in a radiation therapy and had an excellent handleability. The results are presented in Table 1.
(1) Appearance
[Evaluation Criteria]
B: The bolus had a high transparency and was free of bubble inclusion.
D: The bolus had a low transparency.
(2) Dimension
[Evaluation Criteria]
B: The bolus was uniform in thickness and length.
D: The bolus was nonuniform in thickness and length.
(3) Elasticity
[Evaluation Criteria]
B: The bolus had an appropriate elasticity and did not undergo a change such as tearing even when folded by 180 degrees.
D: The bolus had a low elasticity and was torn when folded by 180 degrees.
(4) Heat Resistance
After each bolus was heated in hot water of 60 degrees C. for 30 minutes, the shape and physical properties of the bolus were measured and evaluated according to the criteria described below.
[Evaluation Criteria]
B: The shape and physical properties did not change.
D: The shape and physical properties deteriorated.
(5) Solvent Resistance
After each bolus was washed with ethanol, the shape and physical properties of the bolus were measured and evaluated according to the criteria described below.
[Evaluation Criteria]
B: The shape and physical properties did not change.
D: The shape and physical properties deteriorated.
(6) CT Value
The CT value of each bolus was measured with an X-ray testing device: AQUILION PRIME BEYOND (available from Toshiba Medical Systems Corporation) and evaluated according to the criteria described below.
[Evaluation Criteria]
B: The CT value was 0 or higher but 100 or lower, and close to the body composition.
D: The CT value was higher than 100, and deviated from the body composition.
(7) Storage Stability
After each bolus was stored for 7 days in a sealed state (at 25 degrees C. and 50% RH), the shape and physical properties of the bolus were measured and evaluated according to the criteria described below.
[Evaluation Criteria]
B: The shape and physical properties did not change.
D: The shape and physical properties deteriorated.
(8) Total Evaluation
[Evaluation Criteria]
B: The bolus satisfied the functions to qualify as a bolus, and was very good.
D: The bolus did not satisfy the functions to qualify as a bolus, and was defective.

Example 8

—Preparation of Liquid Material for Producing Bolus—

First, to pure water (400 parts by mass) under stirring, synthetic hectorite (LAPONITE XLG, available from Rock Wood) having a composition $[Mg_{5.34}Li_{0.66}Si_8O_{20}(OH)_4]$ $Na^-_{0.66}$ (30 parts by mass) was added little by little as a mineral, and then 1-hydroxyethane-1,1-diphosphonic acid (0.8 parts by mass) was further added, followed by stirring, to produce a dispersion liquid.

Next, to the obtained dispersion liquid, N,N-dimethylacrylamide (available from Wako Pure Chemical Industries, Ltd.) (40 parts by mass) having been passed through an activated alumina column for removal of a polymerization inhibitor and LIGHT ACRYLATE 9EG-A (available from Kyoeisha Chemical Co., Ltd.) (2 parts by mass) were added as polymerizable monomers.

Next, to the resultant under cooling in an ice bath, a 2% by mass aqueous solution (30 parts by mass) of sodium peroxodisulfate (available from Wako Pure Chemical Industries, Ltd.) in pure water was added, and tetramethyl ethylenediamine (available from Wako Pure Chemical Industries,

TABLE 1

| | | Ex. | | | | | | |
|---|---|---|---|---|---|---|---|---|
| Component (part by mass) | | 1 | 2 | 3 | 4 | 5 | 6 | 7 |
| Mineral | XLG | 30 | 30 | 30 | 30 | 20 | 30 | 30 |
| Polymerizable monomer | N,N-dimethylacrylamide | 40 | 40 | 40 | 20 | 20 | 40 | 40 |
| | LIGHT ACRYLATE 9EG-A | 2 | 2 | 2 | 2 | 2 | 2 | 2 |
| | Acryloylmorpholine | — | — | — | 20 | 20 | — | — |
| Phosphonic acid compound | 1-hydroxyethane-1,1-diphosphonic acid | 1.6 | 1.6 | 1.6 | 1.6 | 1.6 | 1.6 | 1.6 |
| Initiator liquid | Sodium peroxodisulfate (2% aq) | 30 | 30 | 30 | 30 | 30 | 30 | 30 |
| Initiator | Tetramethyl ethylenediamine | 2 | 2 | 2 | 2 | 2 | 2 | 2 |
| Solvent | Glycerin | — | 100 | — | 100 | 100 | — | — |
| | Propylene glycol | — | — | 100 | — | — | — | — |
| Water | Pure water | 400 | 300 | 300 | 300 | 300 | 400 | 400 |
| Coating film | PLASTICOAT #100 | — | — | — | — | — | Thickness (30 micrometers) | — |
| | POVAL 205 | — | — | — | — | — | — | Thickness (30 micrometers) |
| Evaluation result | Appearance | B | B | B | B | B | B | B |
| | Dimension | B | B | B | B | B | B | B |
| | Elasticity | B | B | B | B | B | B | B |
| | Heat resistance | B | B | B | B | B | B | B |
| | Solvent resistance | B | B | B | B | B | B | B |
| | CT value | B | B | B | B | B | B | B |
| | Storage stability | B | B | B | B | B | B | B |
| | Total evaluation | B | B | B | B | B | B | B |

The boluses of Examples 1 to 7 maintained the intended shape even after taken out from the die, and had a homogeneous structure. Moreover, it was easy to confirm close adhesiveness of the boluses with skin, because the boluses had a high transparency. Furthermore, when the boluses were cut with, for example, scissors for size adjustment of the boluses, the boluses did not undergo changes such as excessive tearing.

As in Examples 2 and 3, the boluses in which ion-exchanged water was partially changed to polyvalent alcohol (glycerin and propylene glycol) had an excellent moisture retaining property.

As in Examples 6 and 7, the boluses provided with a coating film on the surface had an even better moisture retaining property.

Ltd.) (2 parts by mass) and succinic acid (available from Wako Pure Chemical Industries, Ltd.) (2 parts by mass) were further added, followed by stirring and mixing, and then vacuum degassing for 10 minutes. Subsequently, the resultant was subjected to filtration to remove, for example, impurities, to obtain a homogeneous liquid material for producing a bolus.

—Production and Evaluation of Bolus—

Figure 10:
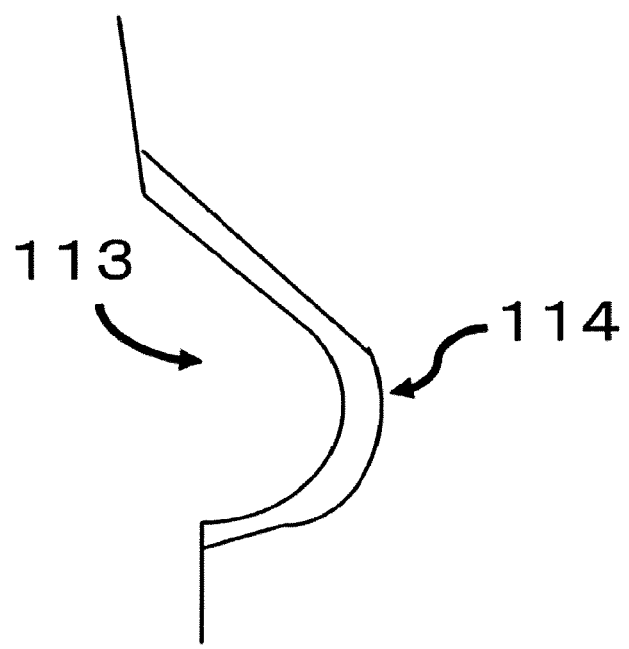
FIG. 10 is a schematic diagram illustrating a state of molding a bolus using a die secured to a chest.

A die 114 suited to the surface of a chest was secured to the surface of the skin of the chest 113 of a subject as illustrated in FIG. 10, and the obtained liquid material for producing a bolus was poured into the die 114 suited to the surface of a chest and subjected to curing reaction at room temperature (25 degrees C.) for 5 minutes. After curing, the die was removed, to directly produce a three-dimensional (3D) bolus for a breast on the chest of the subject.

The three-dimensional (3D) bolus for a breast directly produced on the skin of the subject had a good close adhesiveness and a homogeneous structure.

Hence, it was possible to produce a bolus easily without hurting the subject.

Comparative Example 1

—Preparation of Liquid Material for Producing Bolus—

A liquid material for producing a bolus was produced according to an Example of Japanese Unexamined Patent Application Publication No. 11-221293. That is, polysiloxane serving as a reactive vinyl group-containing main agent (with a viscosity of 1,200 mPa·s at 25 degrees C.) (398.4 parts by mass), methyl hydrodiene polysiloxane serving as a hydrogen-silicon bond-containing cross-linking agent (with a viscosity of 20 mPa·s at 25 degrees C.) (1.6 parts by mass), and a 1% by mass chloroplatinic acid alcohol solution serving as a curing catalyst (0.06 parts by mass) were mixed and stirred, and subsequently degassed completely at room temperature, to product a liquid material for producing a bolus, the liquid material being formed of an addition reaction-type silicone gel.

—Production and Evaluation of Bolus—

An attempt was made to produce a bolus in the same manner as in Example 8, using the obtained liquid material for producing a bolus. However, this liquid material had an extremely high viscosity and was unable to be injected into a die. Hence, it was impossible to produce a bolus.

Comparative Example 2

—Preparation of Liquid Material for Producing Bolus—

A liquid material for producing a bolus was produced according to Example 1 of Japanese Unexamined Patent Application Publication No. 06-47030. That is, polyvinyl alcohol having an average degree of polymerization of about 2,000 and a degree of saponification of 89% by mole was dissolved in water containing 0.9% by mass of NaCl. Here, in order to allow polyvinyl alcohol to be dissolved, polyvinyl alcohol was heated to 60 degrees C. to be dissolved, to prepare a liquid material for producing a bolus.

—Production and Evaluation of Bolus—

An attempt was made to produce a bolus in the same manner as in Example 8, using the obtained liquid material for producing a bolus. However, in the heated state, the liquid material was too hot for the human body and unable to be injected into the die, whereas when cooled, the liquid material transformed into a gel state and was unable to be injected into the die. Hence, it was impossible to produce a bolus.

Comparative Example 3

—Preparation of Liquid Material for Producing Bolus—

A liquid material or producing a bolus was produced according to an Example of Japanese Patent No. 2999184. That is, carrageenan (4.0 g), Locust bean gum (3.0 g), and xanthan gum (3.0 g) were added together, and heated and dissolved at 80 degrees C. for 10 minutes under stirring, to prepare a liquid material for producing a bolus.

—Production and Evaluation of Bolus—

An attempt was made to produce a bolus in the same manner as in Example 8, using the obtained liquid material for producing a bolus. However, in the heated state, the liquid material was too hot for the human body and unable to be injected into the die, whereas when cooled, the liquid material transformed into a gel state and was unable to be injected into the die. Hence, it was impossible to produce a bolus.

Example 9

—Production of Die—

CT data of the surface of a breast of a patient (treatment recipient) was converted into data for three-dimensional (3D) printing. Based on this data, a male the 121 and a female die 122 for a three-dimensional bolus for a breast as illustrated in FIG. 11 and FIG. 12 were produced, using AGILISTA available from Keyence Corporation as an inkjet stereolithography apparatus.

—Preparation of Liquid Material for Producing Bolus—

First, to pure water (200 parts by mass) under stirring, synthetic hectorite (LAPONITE XLG, available from Rock Wood) having a composition $[Mg_{5.34}Li_{0.66}Si_8O_{20}(OH)_4]Na^-_{0.66}$ (14 parts by mass) was added little by little as a layered clay mineral, and then 1-hydroxyethane-1,1-diphosphonic acid (0.7 parts by mass) was further added, followed by stirring, to produce a dispersion liquid.

Next, to the obtained dispersion liquid, acryloylmorpholine (available from KJ Chemicals Corporation) (18 parts by mass) having been passed through an activated alumina column for removal of a polymerization inhibitor and LIGHT ACRYLATE 9EG-A (available from Kyoeisha Chemical Co., Ltd.) (1 part by mass) were added as polymerizable monomers.

Next, to the resultant under cooling in an ice bath, a 2% by mass aqueous solution (14 parts by mass) of sodium peroxodisulfate (available from Wako Pure Chemical Industries, Ltd.) in pure water was added, and tetramethyl ethylenediamine (available from Wako Pure Chemical Industries, Ltd.) (1 part by mass) was further added, followed by stirring and mixing, and then vacuum degassing for 10 minutes. Subsequently, the resultant was subjected to filtration to remove, for example, impurities, to obtain a homogeneous liquid material for producing a bolus.

—Production of Three-Dimensional Bolus for Breast—

The male die 121 and the female die 122 produced previously were combined with each other as illustrated in FIG. 13, to form a gap 123 between both. The liquid material for producing a bolus was poured into the gap 123, capped for sealing, and subjected to curing reaction at room temperature for 6 hours. After curing, the resultant was taken out from the die and washed with water, to obtain a three-dimensional bolus 124 for a breast.

Example 10

A three-dimensional bolus for a breast was produced in the same manner as in Example 9, except that 50 parts by mass out of 200 parts by mass of pure water was changed to glycerin, unlike in Example 9.

Example 11

A three-dimensional bolus for a breast was produced in the same manner as in Example 10, except that 10 parts by mass out of 18 parts by mass of acryloylmorpholine was changed to N,N-dimethylacrylamide (available from Wako Pure Chemical Industries, Ltd.), unlike in Example 10.

Example 12

PLASTICOAT #100 (available from Daikyo Chemical Co., Ltd.) was coated over the surface of the bolus produced in Example 9 by a dip coating method, to form a coating film having a thickness of 30 micrometers.

Comparative Example 4

A liquid material for producing a bolus was produced according to Example 1 of Japanese Unexamined Patent Application Publication No. 06-47030. That is, polyvinyl alcohol having an average degree of polymerization of about 2,000 and a degree of saponification of 89% by mole was dissolved in water containing 0.9% by mass of NaCl. Here, in order to allow polyvinyl alcohol to be dissolved, polyvinyl alcohol was heated to 60 degrees C. to be dissolved. This liquid material was injected into a the in the same manner as in Example 9 for object production and subjected to freezing/thawing nine times, to produce a bolus.

Comparative Example 5

A liquid material or producing a bolus was produced according to an Example of Japanese Patent No. 2999184. That is, carrageenan (4.0 g), Locust bean gum (3.0 g), and xanthan gum (3.0 g) were added together, and heated and dissolved at 80 degrees C. for 10 minutes under stirring. This liquid material was injected into a die in the same manner as in Example 9 for object production, and cooled, to produce a bolus.

<Evaluation>

The following test items of the three-dimensional boluses for a breast produced in Examples 9 to 12 and Comparative Examples 4 and 5 were evaluated. The results are presented in Table 2.

(1) Appearance
[Evaluation Criteria]
B: The bolus had a high transparency and was free of bubble inclusion.
C: The bolus had a slightly low transparency.
D: The bolus had a low transparency.
(2) Dimension
[Evaluation Criteria]
B: The bolus was uniform in thickness and length.
D: The bolus was nonuniform in thickness and length.
(3) Elasticity
[Evaluation Criteria]
A: The bolus had an appropriate elasticity and did not undergo a change such as tearing even when folded by 180 degrees.
B: The bolus had an appropriate elasticity.
D: The bolus had a low elasticity and was torn when folded by 180 degrees.
(4) Heat Resistance
After each bolus was heated in hot water of 60 degrees C. for 30 minutes, the shape and physical properties of the bolus were measured and evaluated according to the criteria described below.
[Evaluation Criteria]
B: The shape and physical properties did not change.
D: The shape and physical properties deteriorated.
(5) Solvent Resistance
After each bolus was washed with ethanol, the shape and physical properties of the bolus were measured and evaluated according to the criteria described below.
[Evaluation Criteria]
B: The shape and physical properties did not change.
C: The bolus slightly swelled.
D: The shape and physical properties deteriorated.
(6) CT Value
The CT value of each bolus was measured with an X-ray testing device: AQUILION PRIME BEYOND (available from Toshiba Medical Systems Corporation) and evaluated according to the criteria described below.
[Evaluation Criteria]
B: The CT value was 0 or higher but 100 or lower, and close to the body composition.
D: The CT value was higher than 100, and deviated from the body composition.
(7) Storage Stability
After each bolus was stored for 7 days in a sealed state (at 25 degrees C. and 50% RH), the shape and physical properties of the bolus were measured and evaluated according to the criteria described below.
[Evaluation Criteria]
A: The shape and physical properties did not change.
B: The bolus did not undergo shape change, but became slightly dry (within a weight change rate of 3%).
D: The shape and physical properties deteriorated.

TABLE 2

|  | Appearance | Dimension | Elasticity | Heat resistance | Solvent resistance | CT value | Storage stability |
| --- | --- | --- | --- | --- | --- | --- | --- |
| Ex. 9 | B | B | B | B | B | B | B |
| Ex. 10 | B | B | B | B | B | B | A |
| Ex. 11 | B | B | A | B | B | B | B |
| Ex. 12 | B | B | B | B | B | B | A |
| Comp. Ex. 4 | C | B | B | D | C | B | B |
| Comp. Ex. 5 | B | B | B | D | C | B | B |

Example 13

—Preparation of Liquid Material for Producing Bolus—

First, to pure water (165 parts by mass) under stirring, synthetic hectorite (LAPONITE XLG, available from Rock Wood) having a composition [Mg$_{5.34}$Li$_{0.66}$Si$_8$O$_{20}$(OH)$_4$] Na$^-_{0.66}$ (17 parts by mass) was added little by little as a layered clay mineral, followed by stirring for 3 hours, to produce a dispersion liquid. Subsequently, to the resultant, 1-hydroxyethane-1,1-diphosphonic acid (available from Tokyo Chemical Industry Co., Ltd.) (0.7 parts by mass) was added, followed by further stirring for 1 hour. Subsequently, to the resultant, glycerin (available from Sakamoto Yakuhin Kogyo Co., Ltd.) (30 parts by mass) was added, followed by stirring for 10 minutes.

Next, to the obtained dispersion liquid, acryloylmorpholine (available from KJ Chemicals Corporation) (17 parts by mass) having been passed through an activated alumina column for removal of a polymerization inhibitor, N,N-dimethylacrylamide (available from Wako Pure Chemical Industries, Ltd.) (4 parts by mass), and LIGHT ACRYLATE 9EG-A (available from Kyoeisha Chemical Co., Ltd.) (1 part by mass) were added as polymerizable monomers. To the resultant, EMULGEN SLS-106 (available from Kao Corporation) (1 part by mass) was added as a surfactant and mixed.

Next, to the resultant under cooling in an ice bath, a 4% by mass methanol solution (2.4 parts by mass) of a photopolymerization initiator (IRGACURE 184, available from BASF) was added, followed by stirring and mixing, and then vacuum degassing for 20 minutes. Subsequently, the resultant was subjected to filtration to remove, for example, impurities, to obtain a liquid material for producing a bolus.
—Preparation of Support Forming Liquid Material—

Urethane acrylate (available from Mitsubishi Rayon Co., Ltd., product name: DIABEAM UK6038) (10 parts by mass), neopentyl glycol hydroxypivalic acid ester di(meth) acrylate (available from Nippon Kayaku Co., Ltd., product name: KAYARAD MANDA) (90 parts by mass) as a polymerizable monomer, and 1-hydroxycyclohexylphenyl ketone (available from BASF, product name: IRGACURE 184) (3 parts by mass) as a polymerization initiator were subjected to dispersion treatment using a homogenizer (available from Koki Holdings Co., Ltd., HG30) at a rotation number of 2,000 rpm until a homogeneous mixture was obtained. Subsequently, the mixture was subjected to filtration to remove, for example, impurities, and finally subjected to vacuum degassing for 10 minutes, to obtain a homogeneous support forming liquid material.
—Production of Three-Dimensional (3D) Bolus—

The liquid material for producing a bolus and the support forming liquid material were filled into two inkjet heads (available from Ricoh Industry Company, Ltd. GEN4) of a three-dimensional printer 10 of an inkjet type as illustrated in FIG. 15, and discharged for film formation.

For object production, CT data of the surface of a breast of a patient (treatment recipient) was converted into data for 3D printing in the same manner as in Example 9. Based on this data, a bolus was produced.

The liquid material for producing a bolus and the support forming liquid material were cured by irradiation of a light volume of 350 mJ/cm$^2$ with an ultraviolet ray irradiator (available from Ushio Inc., SPOT CURE SP5-250DB), to produce a bolus and a support.

After object production, the bolus 17 and the support 18 were pulled in the horizontal direction and detached from each other as illustrated in FIG. 16. As a result, the support 18 was detached as an integral body, and the bolus 17 was able to be easily taken out. In this way, the three-dimensional bolus for a breast was produced.

Example 14

A three-dimensional bolus for a breast was produced in the same manner as in Example 13, except that 0.5 parts by mass out of 1 part by mass of LIGHT ACRYLATE 9EG-A (available from Kyoeisha Chemical Co., Ltd.) in the liquid material for producing a bolus was changed to N,N-methylene bisacrylamide (available from Wako Pure Chemical Industries, Ltd.), unlike in Example 13.

Example 15

POVAL 205 (available from Kuraray Co., Ltd.) was coated over the surface of the three-dimensional bolus for a breast produced in Example 13 by a dip coating method, to form a coating film having a thickness of 30 micrometers.

Example 16

Using a three-dimensional printer of a stereolithography type illustrated in FIG. 17, the liquid material for producing a bolus used in Example 13 was cured by irradiation of a light volume of 350 mJ/cm$^2$ with a laser (available from COHERENT, with a wavelength of 375 nm), to produce a three-dimensional bolus for a breast.

<Evaluation>

Various properties of the boluses produced in Examples 13 to 16 were evaluated in the same manners as in Example 9. The results are presented in Table 3.

TABLE 3

|  | Appearance | Dimension | Elasticity | Heat resistance | Solvent resistance | CT value | Storage stability |
|---|---|---|---|---|---|---|---|
| Ex. 13 | B | B | A | B | B | B | B |
| Ex. 14 | B | B | A | B | B | B | A |
| Ex. 15 | B | B | A | B | B | B | A |
| Ex. 16 | B | B | A | B | B | B | B |

Aspects of the present disclosure are as follows, for example.

<1> A bolus including
a hydrogel,
wherein the hydrogel includes water, a polymer, and a mineral, and
wherein the bolus is applied to a patient who receives a radiation therapy.
<2> The bolus according to <1>,
wherein the bolus has a shape conforming to a body surface of the patient, the body surface being a target of radiation irradiation.
<3> The bolus according to <1>,
wherein the bolus has a radiation transmittance distribution matching an affected part of the patient.
<4> The bolus according to any one of <1> to <3>,
wherein the bolus includes a coating film over a surface of the bolus.
<5> The bolus according to any one of <1> to <4>, further including an organic solvent.
<6> The bolus according to <5>,
wherein the organic solvent is a polyvalent alcohol.
<7> The bolus according to <6>,
wherein the polyvalent alcohol is at least any one of glycerin and propylene glycol.
<8> The bolus according to any one of <5> to <7>,
wherein a content of the organic solvent is 10% by mass or greater but 50% by mass or less relative to a total amount of the bolus.
<9> The bolus according to any one of <1> to <8>,
wherein the mineral is a layered clay mineral.

<10> The bolus according to <9>,
wherein the layered clay mineral is hectorite.
<11> The bolus according to any one of <1> to <10>,
wherein the bolus includes the hydrogel formed by the water being contained in a three-dimensional network structure formed by the polymer and the mineral being combined with each other.
<12> A method for producing a bolus, the method including producing a bolus using a liquid material for producing a bolus, wherein the liquid material includes water, a mineral, and a polymerizable monomer.
<13> The method for producing a bolus according to <12>, wherein the liquid material for producing a bolus includes a polymerization initiator.
<14> The method for producing a bolus according to <13>, wherein the polymerization initiator is any one of a thermal polymerization initiator and a photopolymerization initiator.
<15> The method for producing a bolus according to <12>, wherein the liquid material for producing a bolus includes a phosphonic acid compound.
<16> The method for producing a bolus according to any one of <12> to <15>,
wherein the method produces the bolus by pouring the liquid material for producing a bolus into a die and curing the liquid material.
<17> The method for producing a bolus according to <16>, wherein the method secures the die to a surface of a skin of an affected part of a patient, pours the liquid material for producing a bolus into the die, and cures the liquid material.
<18> The method for producing a bolus according to <16> or <17>,
wherein the method produces the die using a three-dimensional printer.
<19> The method for producing a bolus according to any one of <12> to <15>,
wherein the method directly produces a bolus using the liquid material for producing a bolus and a three-dimensional printer.
<20> The method for producing a bolus according to <19>, wherein the three-dimensional printer is any one of a three-dimensional printer of an inkjet type and a three-dimensional printer of a stereolithography type.

The bolus according to any one of <1> to <11> and the method for producing a bolus according to any one of <12> to <20> can solve the various problems in the related art and achieve the object of the present disclosure.

What is claimed is:
1. A bolus, comprising:
a hydrogel comprising:
 water,
 a synthetic polymer obtained by polymerizing at least one polymerizable monomer,
 a mineral, and
 a phosphonic acid compound,
wherein the bolus is adapted to function as a bolus applied to a patient who receives a radiation therapy.

2. The bolus according to claim 1, wherein the bolus has a shape conforming to a body surface of the patient, the body surface being a target of radiation irradiation.

3. The bolus according to claim 1, wherein the bolus has a radiation transmittance distribution matching an affected part of the patient.

4. The bolus according to claim 1, further comprising:
a coating film over a surface of the hydrogel.

5. The bolus according to claim 1, wherein the hydrogel further comprises:
an organic solvent.

6. The bolus according to claim 5, wherein the organic solvent comprises a polyvalent alcohol.

7. The bolus according to claim 1, wherein hydrogel comprises the water contained in a three-dimensional network structure formed by combining the synthetic polymer and the mineral.

8. A method for producing a bolus, the method comprising forming a bolus from a liquid material comprising water, a mineral, a polymerizable monomer, a polymerization initiator, and a phosphonic acid compound.

9. The method for producing a bolus according to claim 8, wherein the polymerization initiator is at least one of a thermal polymerization initiator and a photopolymerization initiator.

10. The method for producing a bolus according to claim 8, wherein the phosphonic acid compound comprises 1-hydroxyethane-1,1-diphosphonic acid.

11. The method for producing a bolus according to claim 8, wherein the forming of the bolus occurs by pouring the liquid material into a die and curing the liquid material.

12. The method for producing a bolus according to claim 11, wherein the die is secured to a surface of a skin of an affected part of a patient, prior to the pouring of the liquid material into the die.

13. The method for producing a bolus according to claim 11, wherein the die is produced using a three-dimensional printer.

14. The method for producing a bolus according to claim 8, wherein the bolus is produced with a three-dimensional printer.

15. The method for producing a bolus according to claim 14, wherein the three-dimensional printer is any one of a three-dimensional printer of an inkjet type and a three-dimensional printer of a stereolithography type.

16. The bolus according to claim 1, wherein the phosphonic acid compound comprises 1-hydroxyethane-1,1-diphosphonic acid.

* * * * *